(12) United States Patent
Hakalehto

(10) Patent No.: US 8,647,862 B2
(45) Date of Patent: Feb. 11, 2014

(54) METHOD OF INCREASING THE GAS-LIQUID INTERFACE IN A FERMENTATION PROCESS

(76) Inventor: Eino Elias Hakalehto, Kuopio (FI)

( * ) Notice: Subject to any disclaimer, the term of this patent is extended or adjusted under 35 U.S.C. 154(b) by 240 days.

(21) Appl. No.: 12/934,649

(22) PCT Filed: Mar. 30, 2009

(86) PCT No.: PCT/FI2009/000040
§ 371 (c)(1),
(2), (4) Date: Sep. 26, 2010

(87) PCT Pub. No.: WO2009/118445
PCT Pub. Date: Oct. 1, 2009

(65) Prior Publication Data
US 2011/0014648 A1    Jan. 20, 2011

(51) Int. Cl.
*C12M 1/14*    (2006.01)
(52) U.S. Cl.
USPC ..................................................... 435/294.1

(58) Field of Classification Search
USPC ....................................................... 435/294.1
See application file for complete search history.

(56) References Cited

U.S. PATENT DOCUMENTS 2,083,347 A    6/1937    Scholler et al.

FOREIGN PATENT DOCUMENTS

GB    486481 A    6/1938

*Primary Examiner* — Rosanne Kosson
(74) *Attorney, Agent, or Firm* — David A. Guerra

(57) ABSTRACT

When using the equipment and method in accordance with this invention, it is possible to implement biotechnological production e.g. in biorefineries in such a way that it is possible to make use of the phenomena of the gas-liquid interface and interfaces between other phases by means of a moving process solution and gas led into it. This way, production and post-treatment methods can also be integrated, and desired acceleration of reactions and cost reductions can be achieved.

20 Claims, 1 Drawing Sheet

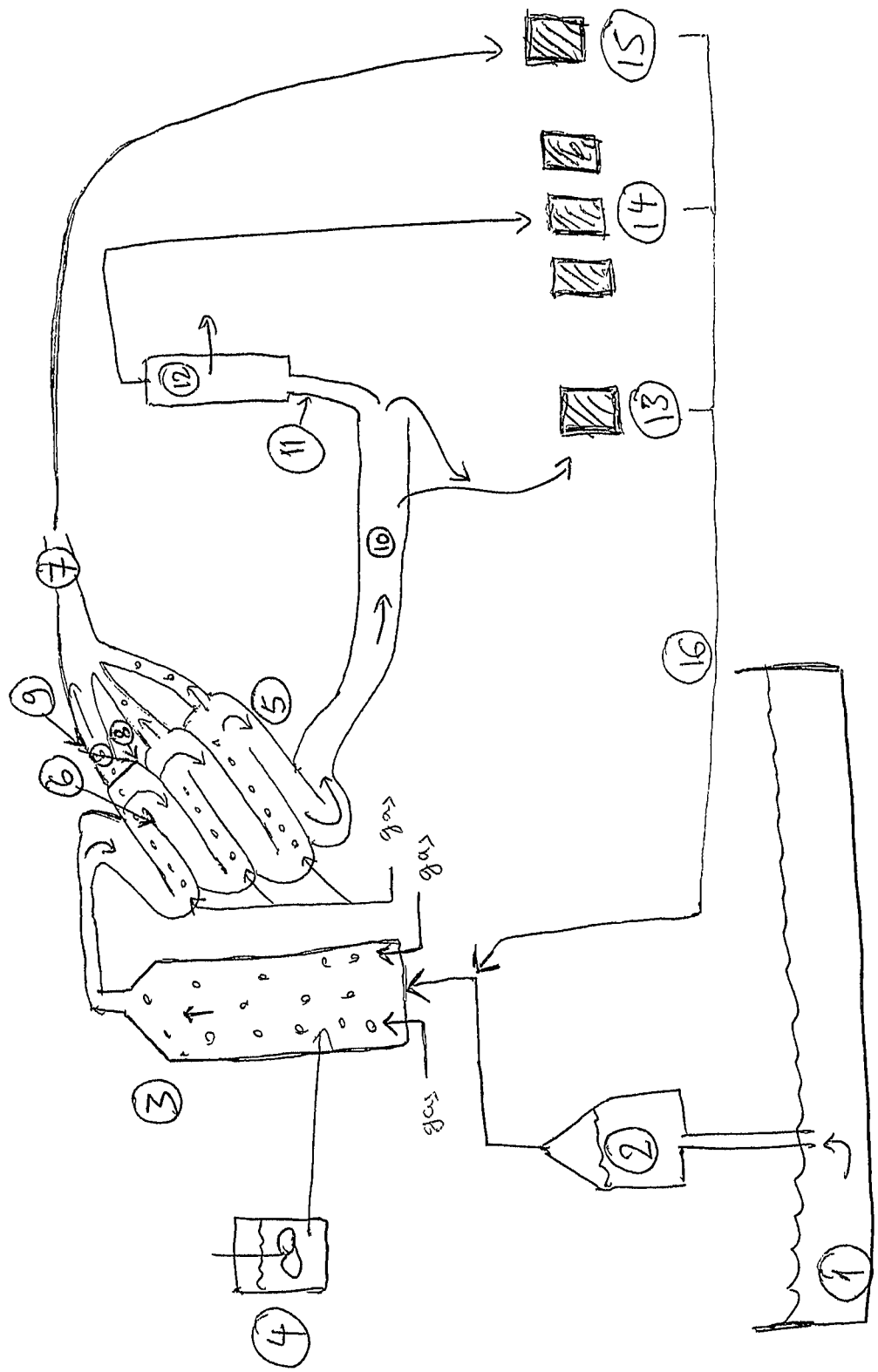

US 8,647,862 B2

METHOD OF INCREASING THE GAS-LIQUID INTERFACE IN A FERMENTATION PROCESS

CROSS-REFERENCE TO RELATED APPLICATIONS

This application is an U.S. national phase application under 35 U.S.C. §371 based upon co-pending International Application No. PCT/FI2009/000040 filed on Mar. 30, 2009. Additionally, this U.S. national phase application claims the benefit of priority of co-pending International Application No PCT/FI2009/000040 filed on Mar. 30, 2009, and Finland Application No. 20080249 filed on Mar. 28, 2008. The entire disclosures of the prior applications are incorporated herein by reference. The international application was published on Oct. 1, 2009 under Publication No. WO 2009/118445.

BACKGROUND OF THE INVENTION

1. Field of the Invention

The present invention relates to a method and equipment for the implementation of a biotechnological process ensuring that the process solution travels in a desired direction.

2. Description of the Prior Art

The field of biotechnology is currently marked by a strong trend of developing new technologies also for high-volume products, such as fuels, chemicals and bioplastics. Consequently, industrial biotechnology and microbiology are rapidly extending their main focus not only into enzymes, drugs and other products with a relatively low production volume but also into new areas of high interest. This development arises from such as concern over the availability and sufficiency of oil and other fossil fuels and their soaring prices, state of the environment and climate development. A positive impact on these issues can be achieved by a more wide-spread use and scope of industrial biotechnology. Biotechnology can also help us to avoid using many high-risk, dangerous or harmful chemicals.

In order to reach the objectives listed above, we will need new technologies for implementing biotechnical reactors, or bioreactors or fermentors, in a novel way, efficiently and optimally. Similarly, the downstream processing and recovery of products need to be developed. In order to reach optimal results in these tasks, or performing bioreactions in reactors and simultaneous or subsequent post-treatment processes, advanced measurement technology, process control and modeling are needed.

Biotechnology solutions typically build on biomass based raw materials, which often can be organic waste of various types. Plant biomass is another typical raw material. In this case, plants with high sugar or starch content can be used. On the other hand, the use of plant materials, such as cellulose, hemicellulose and lignins from wood materials has also been envisioned, and research and production projects of this type have already been realized. When using these macromolecules as sources of carbon and energy for microbial processes, it is usually necessary to hydrolyse them, or subject them to other types of physical, chemical or enzymatic treatment. This preliminary treatment enables an efficient use of the chemical energy bound in these materials for microbial growth and product formation. Lots of these plant-based macro-molecules or polymers are available in the nature, not to mention many waste materials. When using these, it may often be beneficial to add such as nitrogen components in the process or process solution as a source of nitrogen for the microbes, or various types of vitamins or other growth factors vital for the microbe in the process.

Other factors important for microbial growth and function include adjustments for a favorable physicochemical parameters of the process and for compensating changes caused by the microbe itself, thus eliminating any risks leading to drawbacks in the microbe growth, process or product formation. Various environmental factors that need to be taken into consideration in optimization include temperature, pH, partial pressures of oxygen and other gases, osmolarity, viscosity of the process solution etc. Many of these properties also play a role in the downstream processing and recovery of products.

Normally, a bio-reaction or fermentation takes place in a solution as a submerged cultivation: microbes take substances from the process solution, and the products are also formed in the solution. In case the product is the actual microbe cell material, this needs to be separated from the process solution and recovered using different types of downstream processing and purification methods. Microbe cells or enzymes, or other corresponding biocatalysts performing a reaction, may occur freely in the process solution. Often they may also be attached to a carrier material or carrier phase, i.e. be immobilized into or on that carrier. This often crucially extends the period of the biocatalyst usage and considerably increases its tolerance for various environmental pressures and stresses compared to a non-immobilized biocatalyst. In some cases, immobilization also facilitates the downstream.

When using microbes, the bioprocess often achieves an advantage if complex reaction pathways are avoided. Especially, when using microbes that assimilate or have the ability to fix atmospheric nitrogen, these advantages are highlighted. In some cases, biocatalyst properties can be improved by means of genetic manipulation, but in this case, close attention should be paid to health-related and ecological considerations. At best, the use of microbes considerably reduces the formation of harmful wastes.

Processes developed by the assistance of microbes are often called bio-refineries, especially when they are meant to complement or replace petrochemical industry. One benefit of these activities is that a number of products and processes can be run simultaneously. On the other hand, the same equipment can be used for different production and downstream processes. This may reduce the investment costs in biotechnical processes compared to those of chemical or petrochemical industries. However, additional costs in biotechnology may incur from demand for aseptics, which places high demands to the quality of materials, throughputs etc. Similarly, heterogeneity of the process solution may increase the costs significantly. If case waste is used as raw material, on the other hand, its negative price may have a positive effect on the total costs of the process, as well as multiple effects of positive environmental impacts or reductions in the emissions.

Often problematic in terms of the total result of a bioprocess is the fact that the product formation or production does not take place at a rate high enough. This is causing diluted process solutions or product mixtures, leading into high expenses in product recovery and purification. Similarly, in case the product is gaseous or a vaporizing substance and it can be separated by such means as distillation, the concentrations and production rate often remain low. In these situations, an adequate product concentration cannot be obtained sufficiently fast, which has a negative impact on the cost-effectiveness of the whole process. The risks of contamination by undesirable microbes and consequently great losses are increased. In order to optimize the entire process, it is often sensible to model it, allowing the simulation of the effects of various regulations on the reaction parameters in the process solution through the model. These regulations cannot, however, replace on-line measurements that yield accurate information on the process that is under way.

Placing different types of probes and sensors in the right areas in the bioreactor, or in an adequate number of locations in the various sections of the process solution, may emerge as a problem. In high-volume production plants, this may end up being highly expensive, and the sensor throughputs may cause contamination problems. Consequently, obtaining accurate data on the entire bioreactor or the situation of the whole process solution for modeling it and its biochemical regulations may be difficult. In order to resolve this technical issue, too, new types of bioreactors are needed. In the production of biofuels, biochemicals or other large-volume products, these problems are often emphasized, as is the fact that the high requirements placed on various materials in the bioprocess, such as steel quality, will increase the overall costs.

Many quantitative parameters in bioreactors are measured continuously. These may include monitoring not only the above-mentioned physicochemical values, such as temperature, pH and oxygen partial pressure, but also measurements of substrate and end product concentrations. These give important data on the progress of the process for its regulation, use of raw materials and product formation. With respect to these measurements, it is also essential to get a true picture of the whole process solution or bioreactor status.

Because bioreactor raw materials and end products usually are heterogeneous, a type of platform thinking in the biochemical, biotechnical and microbiological sense is useful. Certain organisms and their metabolic pathways offer an opportunity to vary the production, raw material use, production directions as well as the formation and recovery of different products. According to this way of thinking, the bioreactor or bioprocessor in a certain sense is an ecosystem subject to the laws of microbiology, which can also be utilized in a technological sense. The basis of all technological design and construction in macroscopic scale should lie in understanding of microscopic phenomena and observation of microbial interaction. What we need are new types of technological entities taking into account the phenomena occurring at the interface between the living biological material and engineering technology. These entities comprise of comprehensive measurement and regulation methods, production control taking into account the whole reactor volumes, more efficient movement of materials, and development of the recovery, and its integration into the production method, among other things. In this wider sense, developing bioreactors will be the most important task of bioprocess technology in the near future.

Various bioreactor and fermentor solutions include Stirred Tank Reactors with mechanical stifling, static fermentors, equipment for cultivation and production reactions on solid or semi-solid beds (e.g. techniques used for cultivating plant and animal cells), columns of various types (that may feature bubbles), air lift reactors, hollow fibre fermentors, basins and containers (with or without stirring), and bioreactors with immobilized biocatalysts (packed-bed or fluidized-bed types). In this application, the terms reactor, bioreactor and fermentor refer to equipment in which biochemical production or a reaction is performed. The fermentation or bioreaction may be of a fed-batch type or a continuous one. The former starts at a certain point, subsequently going through the whole process, mainly with the same raw materials; whereas in a continuous reaction, new raw materials are continuously fed in and correspondingly some part of the used materials removed. The problems inherent in the latter type of reactor, however, include a low level of utilization of the raw materials, even if some speeding up of the reaction is usually possible to accomplish e.g. in a chemostat type fermentor. Currently, majority of large-scale process solutions are of the so-called fed-batch type, in which the raw materials (nutrient medium for microbes or other cells) are added in a number of batches during the bioreaction into the original process solution (and the products thus formed often are also recovered in batches). This is naturally not applicable to acid or base additions used to regulate the fermentor or additions of other additives or regulators, but the addition of the actual main process raw materials only.

The objective of industrial microbiology and process biotechnology is to form the desired product, such as a cell mass, enzyme, chemical, polymer or fuel, by an energetically advantageous reaction in a bioreactor, making use of the biocatalysis of microbes or other cells (or filamentous growth forms) or the enzymes of the above-mentioned organisms. The biocatalyst may also be developed or refined through genetic recombination methods, in which case various safety considerations and risks should be taken into account with special care in the development of the biocatalysts, for example regarding the risks of unintentionally transferring genetic material. A part of a cell or cells may also sometimes work as a biocatalyst. What is essential is producing the desired products with lower amounts of reaction energy than in a corresponding chemical or physical reaction would be achievable. Bioreactors and biocatalysts may, in such cases as in polymerase industry, contribute to the production of substances and structures that cannot be achieved chemically by means of traditional synthesis. Similarly, by combining different microbes or organisms together (or with various enzymes) in the one and same reaction, process, or technological platform, such as in efficiently breaking down materials otherwise difficult to degrade. This phenomenon of accomplishing degradation as a result of the combined action of e.g. microbes, in a case which any individual microbe could not manage alone, is referred to as commensalism.

Cells that are used as biocatalysts are usually cultivated in the reactor until the process or reaction progresses up to a certain point. The cultivation may take place in one part of the reactor, or in case of reactors connected in a series, in some of the reactions, or during a temporary and limited period in the reaction. In any case, what often may become a problem is the fact that the growth of microbes or other cells requires different conditions from the formation of the actual product. Many antibiotics and enzymes, for example, are secondary metabolites, which can be formed after an active growth phase only. In this case, one must be able to prevent the formation—after the growth or other previous reaction or treatment phases—of components preventing or slowing down the actual product formation, also by the biocatalysts themselves. Contaminating microbes occurring in the raw material or emerging during the process can also in a more or less crucial manner impede the action of the biocatalyst, and also the growth of the actual process microbe and performance of production.

In terms of the overall cost-effectiveness of a bioreactor, it is also vital to ensure that the various nutrients are efficiently used and that the microbe's own control mechanisms, such as end product inhibition or catabolite repression, do not significantly reduce reaction efficiency. This can be influenced by using mixed instead of pure microbial cultures, or for example by removing substances potentially inhibiting, such as the end products or other products (such as metabolic wastes products), from forming into the process solution during the entire reaction or inside the reactor, as soon as these are formed. They can for example be recovered by means of sieving, filtering, two-phase fermentation, chromatography or vaporization as well as evaporation (e.g. distillation). In many techniques, vacuum suction can be used. Bacteria belonging to the species *Escherichia coli* are industrially very important. In their cultivation the use of a fed-batch reactor reduces the inhibitory acetate formation in so-called overflow metabolism, which does not support bacterial growth. The use of this reactor type also reduces catabolite repression compared to ordinary fed-batch cultivation.

An attempt can also be made to actively influence the regulatory genetic elements of microbes by adding certain extra nutrients or additives, or activating or inhibitory factors, to a specific cultivation or reaction phase. In a traditional bioreactor, this usually affects the whole reaction mixture, as stifling usually spreads the substance in question everywhere in the process solution. In fact, this kind of conduct may even take place during normal regulation of fermentation pH or temperature. The optimum temperature for growth, for example, may be different from the optimum one for the product formation. Similarly, e.g. the bacteria performing the 2,3-butanediol fermentation may grow fast in aerobic conditions, but the best yield of butanediol is achieved in microaerobic conditions.

In a biotechnical reaction, the impact of products separating from the catalyst on regulation systems and product formation is emphasized, especially in case their removal from the vicinity of cells or another catalyst is prolonged, for example because of diffusion restrictions of the substrate solution or compounds in it. Similarly, the impact of metabolic wastes that inhibit or slow down the action of the biocatalyst is often highlighted because of diffusion restrictions. They also have an influence on the cells' nutrients supply and/or substrate intake. The diffusion of various gases also plays an important role, such as in influencing the availability of oxygen to aerobic organisms. In addition to oxygen, other gases may also be highly significant (Hakalehto et al. 2007).

Of various organisms that are useful in biotechnology, spore-forming aerobic and anaerobic bacteria could be mentioned, such as representatives of the genus *Bacillus* in the aerobic group, and in the anaerobic group most importantly the ones belonging to the genus *Clostridium*, the latter of which include bacteria performing acetone-butanol fermentation, or butyric acid bacteria. Of the genus *Bacillus*, thermophilic bacteria are particularly important in many applications, as at high temperatures their metabolism, and thus also product formation, usually speeds up considerably. Facultative anaerobic bacteria, such as *E. coli* (mixed acid fermentation) and *Klebsiella* sp. or other enterobacterial species (carrying out 2,3-butanediol fermentation), methane producers and methylotrophic bacteria, various types of degraders, e.g. the genus *Pseudomonas* (aerobic), and many others also are of interest for the chemical and polymer industries. Of the yeasts, such as *Candida* sp. and *Saccharomyces cerevisiae* are commonly used for various types of fermentation, for example ethanol fermentation, and production of animal feed. Moulds and filamentous actinomycetes perform a number of special biocatalytic functions. They are, for instance, important producers of antibiotics, and they form many hydrolytic enzymes, which are used for the hydrolysis of macro-molecules in biomasses.

Various biotechnical modeling may focus on enzymatic kinetic reactions, as well as on mass transfer properties as regarding substrates, products, biocatalysts and wastes in the bioreactor and process solution. From the perspective of regulation, in order to prevent the formation of inhibitory by-product flows, it is important that the raw material in the reactor is converted into the desired products in its entirety.

The properties of enzymes (and also cells) as biocatalysts can be listed as specificity, selectivity, specific speed of product formation, nutrient intake rate and stability of the biocatalyst. Understanding mass transfer properties of substances requires studies on the mechanics and hydraulic properties of liquids. The boiling temperatures and other physical and chemical properties of various substances must be determined. It is also important to know the temperature limits and optimums for growth and product formation of microbes taking part in the reaction, as well as the corresponding values for the pH, dissolved oxygen and other environmental parameters. By using means of fluorescence spectra, we can measure the concentrations of sugars, various ions, growth factors or carbon dioxide (e.g. for monitoring of the breathing of the cells), which can be used to collect important data for the running the process. Extending all these measurements to the whole reactor volumes and process solution, however, often becomes overwhelmingly expensive. It is also important to determine the heat transfer properties for the entire reaction e.g. by using a thermal camera system. Studies on heat transfer and gas diffusion conditions may yield information on such parameters as the predictable possibilities of biofilm formation in various parts of the reactor. Liquid flows and movements can also be simulated by computer modeling. The importance of determining all these process parameters is only increasing as the process is scaled up. In larger volumes, arranging heat regulation and even distribution of the various substances is more difficult than on the lab scale. The MFA procedure ("Metabolic Flux Analysis") based on knowledge of all biochemical pathways could be used to take into account all metabolic pathways and transformations through modeling them.

In addition to modeling, appropriate measurements are essential in order to control the events on real time and in real-life conditions. Predicting or monitoring different biological phenomena in particular by only theoretical modeling may become an insurmountable obstacle, and even parallel or repeated measurements may produce widely variable results due to the special features of different biological materials. In this connection, we must take into account that process solutions or suspensions are not usually homogeneous microscopically, but contain cells and other particles, the behavior being a very challenging task to model. In terms of practical reactor design, a great degree of homogeneity in the process solution is highly important, at least during a specific process phase of particular importance. Extending the measurements into the entire reaction space may involve difficulties, and the same is true with the arrangements of throughputs, which as such haven an impact on what happens in the process solution, as well as increase contamination risk and bring up the costs.

When biotechnology is needed to produce chemical components of a relatively low value on a large scale, new technical solutions are required. In addition to measurements, modeling and arrangements for mass transfers, the most important task is organizing downstream processing and product recovery. This can often be integrated into the production process. The available methods include distillation, membrane filtration, sedimentation, sieving, centrifugation, evaporation, ultra-filtering and various chromatographic methods. These can be combined, and different products recovered in the same process.

SUMMARY OF THE INVENTION

The present invention essentially comprises a method to implement a biotechnical microbial process and to form a product. The method includes the implementing of a biotechnical microbial process to a product fluid. Then traveling a process solution in a predetermined direction. Lastly, feeding a gas mixture into the process solution, wherein the gas mixture is anaerobic or oxygen including.

The invention may also include the inoculating a microbial cultivation in the process solution into a production fermentor, into which the gas mixture is led into at one or more points. The production fermentor is divided into sections by inclined partitions, in which the process solution travels obliquely upwards and obliquely downwards. There are, of course, additional features of the invention that will be described hereinafter and which will form the subject matter of the claims attached.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a schematic view of the preferred embodiment of the microbiological production method and equipment constructed in accordance with the principles of the present invention.

The same reference numerals refer to the same parts throughout the various figures.

DETAILED DESCRIPTION OF THE INVENTION

The method and equipment in accordance with this invention typically allow for the implementation of a biotechnological process ensuring that the process solution travels into a desired direction. Various types of tanks, containers and reactors may also be built for preliminary treatments and intermediate phases, in which the process solution remains for some time. However, as the process solution moves on, the desired gas or gas mixture, which may contain oxygen or be anaerobic, is simultaneously led into it. The movement of the process solution may be achieved for example through the action of a pump, and physical phenomena can be utilized in it, such as gravity, hydrostatic pressure, capillary action or diffusion. The movement of the process solution can also be affected by means of a conveyor, belt, wire or similar, causing the process solution to travel with it in a relatively thin layer, such as in a pulp and paper factory. The difference is, however, that the solution travels in a limited space in an optimal way, making it possible to create an environment that is aseptic or more hygienically controlled than it is in an open forest industry process. Similarly, when using the method and equipment in accordance with this invention, the partial pressures and gaseous mixtures of gases in the process solution and in its immediate vicinity can be regulated. This also makes it possible to create desirable gas-liquid interfaces, and reactions may take place in different ways in a process solution where bubbles of various types of gaseous mixtures have been added, or in a similar liquid or suspension. The reactions may also take place in a foaming environment, in which an attempt is further made to speed up the mass transfers and switching of the phase from a gas into liquid or vice versa.

A number of benefits can be achieved by leading gases into the process solution. They can be used to bring raw materials and growth factors for various microbes into the microbe's nutrient medium. The diffusion of gases and nutrients is improved, as wastes that inhibit microbial growth and product formation can be removed faster than before when compared to a sole liquid phase, based on the pressure and temperature differences of various existing or verifiable gases. The absorption of gases and removal of volatile products also affect the temperature conditions of the process solutions and reactor, and these phenomena can be utilized in heat transfers to the various parts of the reactor and solution. A crucial difference of the present invention when compared to e.g. forest industry processes is that as the moving forces of the latter, such as gravity and hydrostatic pressure, work into one direction, the forces associated with gas pressures in the present invention caused by feeding in bubbles of gases into the solution work towards the other, opposite direction. Consequently, at the intersection of these different forces, conditions are formed where the mass transfers are stronger and faster, facilitating biological, biochemical and biotechnical reactions. For one advantageous way of implementing equipment in line with this invention, see FIG. 1.

FIG. 1 shows a raw material collection and distribution basin (1), the volume of which may be considerably larger than that of the actual bioreactor parts. After this basin, one or several reactors, pools or similar (2) intended for preliminary treatment may be placed, from which the process solution is led to the precultivation fermentor (3), into which is added or transfer, an inoculum, from a separate inoculum fermentor or a laboratory culture, or directly from a preserved microbe preparation or similar (4). The precultivation fermentor may be a gas bubble column or equivalent. The inoculum fermentor may be for example a PMEU equipment (Finnoflag Oy, Kuopio and Siilinjarvi, Finland), or an ordinary laboratory fermentor or other microbe cultivation plate or a compostor, in which the cultivation temperature can rise as a consequence of by microbial metabolism up to the thermophilic range. These are only a few examples of precultivation fermentor and transfer fermentor systems built-in and connected to the actual production fermentor on a continuous basis. From a precultivation fermentor, the microbial culture in the process solution is transferred into a specifically built production fermentor or reactor (5). During precultivation and inoculum preparation, aerobic, anaerobic or microaerobic gas insertions can be used. The gas may also be used in the production fermentor, or the gas may be applied differently with respect to its composition, temperature, pressure or flow rate. Together with the gas, substances can be added and volatile or vaporizing substances removed, which may be reaction products, waste materials or other substances. This way, taking an advantage of the intensified diffusion of substances, the restrictions caused by genetic control systems of micro-organisms to biotechnological production may be eliminated or reduced. The reduction of diffusion restrictions also improves the heat transfer properties in various phases and between them. In this application, the production fermentor may be divided by inclined partitions or levels (6) into various sections, in which the process solution sometimes travels obliquely upwards and sometimes obliquely downwards, the total effect, however, being a gradual downward movement (movement in an appropriate direction). In this equipment, different types of spectrophotometric, calorimetric or other measurement and sensor solutions can be integrated, with the added advantage of them being non-invasive. As levels, such as light-permeable plastic or light can be used. Then detection of the measurement results may take place e.g. on the top surface of the level, while the light is produced from underneath (or vice versa).

By pumping or by—other methods, gas can be directed into the process solution at points where the downward travelling direction is replaced by an upward one, and the recovery of gaseous fractions can be extended into the opposite turning points where the process solution starts travelling downwards, through discharge outlets, pipe outlets or similar (7). In order to e.g. regulate pressure or prevent overflow, these can conveniently be closed with semi-permeable membranes (8) or valves (9), or both. Remaining part of the process solution is led to a separation line, for example (10), where some additional fermentation may take place with most importantly the recovery of liquid fractions or, alternatively, solid fractions by using filtering, sieving, two-phase or centrifugal techniques or other methods. To separate out the various phases, precipitation can also be used, which can be extended into or intensified by adding the required substances in the remainder of the process solution. Structurally, the separation line may also be a moving wire or belt, or it can be or become a pipe (11), from which the liquid phase is e.g. led to chromatographic product recovery (12). The various fractions can subsequently be collected into product recovery containers or basins (13-15). These can be delivered to storage. Various fractions can also at least partially be recycled back to the process if necessary (16).

When using the method and equipment in accordance with the present invention, e.g. the following benefits are achieved:
the utilization rate of raw materials improves e.g. because of the great number of separate process phases and the multi-phased nature of the main reaction, as well as because of the combining of the production phase with product recovery;
the diffusion of raw materials, biocatalyst, products and wastes becomes more efficient even in a large total volume of process solution; this increases the efficiency of e.g. recovery and reduces inhibitory tendencies affecting the process and its reactions caused by genetic regulation systems;
the corresponding improvement in the metabolic and heat transfer properties improve microbial growth and product formation, this effect can be achieved in aerobic, anaerobic and microaerobic conditions alike (Hakalehto et al. 2007);
thanks to the increased production rate, the risk of contamination is reduced, which enables the use of less expensive materials and other solutions;
the production microbe used as the biocatalyst can be produced in a preliminary cultivation in a separate facility and transferred into fermentor when the appropriate stage of growth has been achieved;
the relatively thin reaction layers and large surfaces facilitate better arrangements for the of measurements, modeling, adjustments and optimization;
thanks to the high reaction rate, the overall reactor volume can be reduced, resulting in cost savings;
the possibility of also making use of the phenomena on the liquid-gas and gas-solid phase interface, through gassing the process solution can be foamed, in case this improves the results (foam formation can be controlled and restricted if necessary by means of regulating the pressure and additives);
the pressure of gases pumped into the reactors, or fermentors, can be used in substance and heat transfers, and their temperature, pressure, flow rate and composition can be regulated and product recovery intensified, and substances may also be added this way;
different gases can be led into the various sections or layers of the production fermentor as is required during the process run, and the material flow can be optimized;
in the handling and transport of the process solution and product fractions travelling in thin layers, not only gas pressure but also gravity, hydrostatic pressure, capillary action, vacuum suction, and liquid viscosity regulation can be used; and
heat regulation in various reaction phases can be achieved by means of heat exchangers, and heat can be lead from one area to the next, and the microbes' own ability to produce heat can thus be utilized to improve the overall economy of the process.

REFERENCES

E. Hakalehto, J. Pesola, L. Heitto, A. Narvanen, A. Heitto, Aerobic and anaerobic growth modes and expression of type 1 fimbriae in *Salmonella, Pathophysiology* 14(1) (2007) 61-69.

The invention claimed is:

1. A method to improve product yield from a biotechnical microbial process said method comprising the steps of:
  a) adding a culture medium that is a process fluid to a production fermentor, said production fermentor being divided into sections by inclined partitions, in which said process fluid moves obliquely upwards and obliquely downwards;
  b) inoculating a microbial culture in said process fluid into said production fermentor;
  c) moving said process fluid in a predetermined direction;
  d) feeding a gas mixture into said process fluid;
  e) measuring data from a portion of said process fluid moving through said sections of said production fermentor, said data being obtained by at least one sensor placed in at least one of said sections of said production fermentor; wherein said gas mixture is anaerobic and is determined on the basis of said data; and
  f) isolating the product made in at least step (e), wherein said oblique upward and downward movements of said process fluid on said partitions improve said product yield.

2. The method according to claim 1, wherein said process fluid is moved forwards by a method selected from the group consisting of pumping, gravity, hydrostatic pressure, capillary action, and vacuum suction.

3. The method according to claim 1, wherein said process fluid is moved forwards by a belt.

4. The method according to claim 1, wherein said process fluid is moved in said predetermined direction by phenomena selected from the group consisting of leading in of gas, formation of gas, lowering of liquid viscosity in said process solution, and precipitation of solid material.

5. The method according to claim 4, wherein said phenomena take place as a result of an action of at least one microbe.

6. The method according to claim 1, wherein said step of feeding said gas mixture into said process fluid improves mass and heat transfer properties of said process fluid.

7. The method according to claim 6, further comprising the step of regulating said gas composition regarding said propositions of gases in said gas mixture, and the oxygen content of said gas mixture, and wherein said gas mixture is fed to said process fluid from one or more points.

8. The method according to claim 5, wherein said microbe used is cultivated before inoculation in a preliminary treatment fermentor to a growth stage that is predetermined for formation of said product.

9. The method according to claim 7 further comprising the step of recovering said product while said process fluid moves in said predetermined direction.

10. The method according to claim 9, wherein said recovery takes place by distillation.

11. The method according to claim 1, wherein said measurements are spectrophotometric.

12. The method according to claim 11 further comprising the step of recovering said product in a gaseous form while said process fluid is moving in said predetermined direction.

13. The method according to claim 12, wherein said gas mixture is fed to said process fluid by pumping at points where said obliquely downward direction changes to said obliquely upward direction, and gaseous fractions deriving from said process fluid are recovered where said moving direction of said process fluid turns downwards through discharge outlets.

14. The method according to claim 13 further comprising the step of closing said discharge outlets for regulating pressure.

15. The method according to claim 14, further comprising the step of processing said process fluid by adding an inoculum from an inoculum fermentor to said process fluid in a precultivation fermentor before the production phase of feeding said gas mixture into said process fluid.

16. The method according to claim 15, wherein additional product is recovered from a filter between said production fermentor and at least one second vessel, and wherein said second vessel is configured to receive said product-containing process fluid.

17. A method to improve product yield from a biotechnical microbial process, said method comprising the steps of:
   a) feeding a process solution into a first fermentor;
   b) adding an inoculum from a second fermentor to said process solution in said first fermentor to produce a microbial culture in said process solution;
   c) transferring said process solution into said first fermentor in a predetermined direction, wherein said first fermentor is divided into sections by inclined partitions, in which said process solution moves substantially downwards by moving in at least one obliquely upwards direction and then in at least one obliquely downwards direction;
   d) feeding a gas into said first fermentor at one or more points where said downwardly moving direction of said moving process solution changes to said upwardly moving direction, said gas being anaerobic; and
   e) recovering gaseous fractions derived from said process solution where said moving direction of said process solution changes from said obliquely upwards direction to said obliquely downward direction, said gaseous fractions being recovered through discharge outlets; wherein said partitions include at least one sensor for spectrophotometric and calorimetric measurements of said process solution; and
   f) isolating the product made in at least step (d), wherein said oblique upward and downward movements of said process fluid on said partitions improve said product yield.

18. The method according to claim 17 further comprising the step of closing said discharge outlets for regulating pressure.

19. The method according to claim 17, further comprising the steps of:
   g) feeding the remainder of said process solution from said first fermentor to a chromatographic product recovery device; and
   h) recovering liquid fractions derived from said process solution from a filter between said first fermentor and said chromatographic product recovery device said separation line.

20. The method according to claim 19, further comprising the steps of:
   i) collecting said gaseous fractions, and said liquid fractions from said chromatographic product recovery device in at least one product recovery container; and
   j) recycling at least one of said gaseous fractions, and said liquid fractions from said container to said first fermentor.

* * * * *